United States Patent
Ozer et al.

(10) Patent No.: US 11,969,030 B2
(45) Date of Patent: Apr. 30, 2024

(54) INTEGRITY MONITORING FOR FLEXIBLE MATERIAL

(71) Applicant: Arm Limited, Cambridge (GB)

(72) Inventors: Emre Ozer, Buckden (GB); Jedrzej Kufel, Soham (GB); James Edward Myers, Great Wilbraham (GB); Remy Pottier, Grenoble (FR); John Philip Biggs, Cambridge (GB)

(73) Assignee: Arm Limited, Cambridge (GB)

(*) Notice: Subject to any disclaimer, the term of this patent is extended or adjusted under 35 U.S.C. 154(b) by 220 days.

(21) Appl. No.: 17/543,070

(22) Filed: Dec. 6, 2021

(65) Prior Publication Data
US 2023/0172287 A1   Jun. 8, 2023

(51) Int. Cl.
*A41D 1/00* (2018.01)
*A41D 19/015* (2006.01)
*A61F 6/04* (2006.01)
*G01R 31/28* (2006.01)

(52) U.S. Cl.
CPC ........... *A41D 1/002* (2013.01); *A41D 19/015* (2013.01); *A61F 6/04* (2013.01); *G01R 31/2812* (2013.01)

(58) Field of Classification Search
CPC ......... A41D 1/002; A41D 19/015; A61F 6/04; G01R 31/2812; G01N 27/205; A61B 42/30
USPC ........................................................ 340/652
See application file for complete search history.

(56) References Cited

U.S. PATENT DOCUMENTS

| | | | |
|---|---|---|---|
| 5,157,379 A * | 10/1992 | Dennison | A61B 42/30 128/897 |
| 7,683,797 B2 * | 3/2010 | Woodard | G01R 33/02 340/568.2 |
| 10,422,056 B2 * | 9/2019 | Douglas | D03D 15/258 |
| 11,074,795 B1 * | 7/2021 | Neidigk | G01V 3/10 |
| 11,246,213 B2 * | 2/2022 | Longinotti-Buitoni | D06P 1/5285 |
| 2007/0183110 A1 * | 8/2007 | Woodard | G01R 33/02 361/103 |
| 2009/0025819 A1 * | 1/2009 | Douglas | D03D 15/283 139/420 R |

(Continued)

FOREIGN PATENT DOCUMENTS

| WO | 96/04546 | 2/1996 |
|---|---|---|
| WO | 2021/165148 | 8/2021 |

OTHER PUBLICATIONS

Combined Search and Examination Report for GB Application No. 2217495.7 dated Apr. 28, 2023, 6 pages.

*Primary Examiner* — Eric Blount
(74) *Attorney, Agent, or Firm* — NIXON & VANDERHYE P.C.

(57) ABSTRACT

Wearable items and methods of monitoring wearable items are disclosed. The wearable item comprises a flexible base material forming at least a portion of the wearable item, plural conductive traces traversing the flexible base material, and conductivity sensing circuitry coupled to the plural conductive traces. The conductivity sensing circuitry is configured to distinguish conductivity from non-conductivity of the plural conductive traces, and configured to generate a conductivity indication for at least one of the plural conductive traces. The plural conductive traces follow indirect paths across the flexible base material, allowing the flexible material to flex and stretch normally without breaking the conductive traces.

19 Claims, 11 Drawing Sheets

(56) References Cited

U.S. PATENT DOCUMENTS

| | | | |
|---|---|---|---|
| 2014/0070957 A1* | 3/2014 | Longinotti-Buitoni | ..................... A61B 5/02055 340/870.01 |
| 2021/0137183 A1* | 5/2021 | Carter | ................ F21V 33/0008 |

* cited by examiner

INTEGRITY MONITORING FOR FLEXIBLE MATERIAL

TECHNICAL FIELD

The present disclosure relates to flexible materials and in particular to monitoring the integrity of such flexible materials.

DESCRIPTION

The integrity of a flexible material may be essential to its function. For example, a wearable item at least partially formed of a flexible material, such as a glove or another such protective item, may be required to provide a reliable barrier for the user wearing the item. As such the integrity of the flexible material is of key significance to the user and techniques to monitor the integrity are desirable.

SUMMARY

In one example configuration described herein there is a wearable item comprising:
 a flexible base material forming at least a portion of the wearable item;
 plural conductive traces traversing the flexible base material; and
 conductivity sensing circuitry coupled to the plural conductive traces, wherein the conductivity sensing circuitry is configured to distinguish conductivity from non-conductivity of the plural conductive traces, and configured to generate a conductivity indication for at least one of the plural conductive traces,
 and wherein the plural conductive traces follow indirect paths across the flexible base material, such that a conductive trace traversing the flexible base material from a first point to a second point has a trace length which is greater than a direct distance between the first point and the second point.

In one example configuration described herein there is a system comprising:
 a wearable item in accordance with various example configurations described herein; and
 a further wearable item,
 wherein the wearable item and the further wearable item are arranged to be worn by an individual, and wherein the further wearable item is configured to receive the signal indicative of the potential rupture indication and to communicate the signal to the individual.

In one example configuration described herein there is a method of monitoring a wearable item, wherein the wearable item comprises:
 a flexible base material forming at least a portion of the wearable item; and
 a first set of conductive traces and a second set of conductive traces traversing the flexible base material, wherein the first set of conductive traces and the second set of conductive traces follow indirect paths across the flexible base material, such that a conductive trace traversing the flexible base material from a first point to a second point has a trace length which is greater than a direct distance between the first point and the second point,
 the method comprising the steps of:
 applying a test current to the first set of conductive traces;
 detecting a current flow in the second set of conductive traces;
 controlling a set of trace connection switches, each trace connection switch arranged selectively to couple a pair of conductive traces comprising a first conductive trace of the first set of conductive traces and a second conductive trace of the second set of conductive traces; and
 generate a conductivity indication for the pair of conductive traces.

BRIEF DESCRIPTION OF THE DRAWINGS

The present invention will be described further, by way of example only, with reference to embodiments thereof as illustrated in the accompanying drawings, in which.

DESCRIPTION OF EXAMPLE EMBODIMENTS

Figure 1:
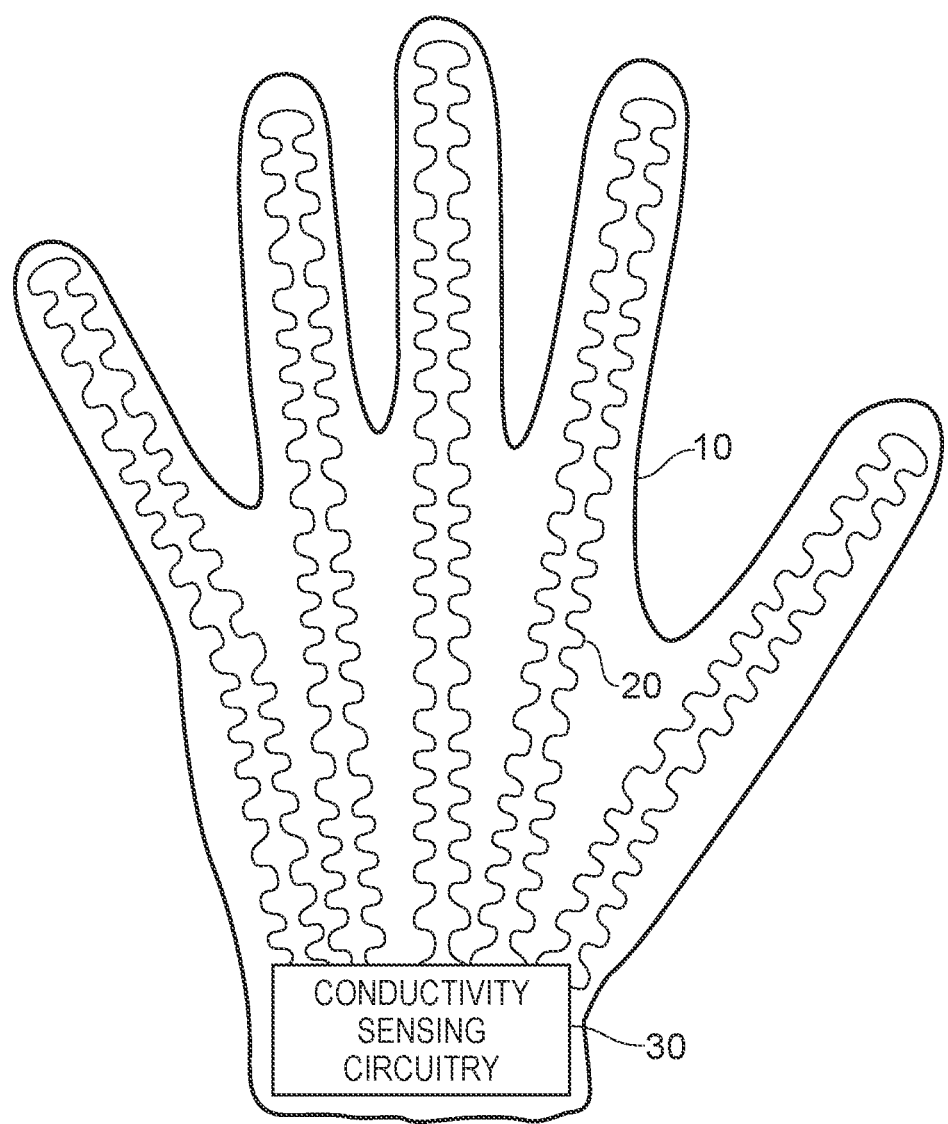
FIG. 1 schematically illustrates a wearable item in the form of a glove in accordance with some example configurations.

Before discussing the embodiments with reference to the accompanying figures, the following description of embodiments is provided.

In accordance with one example configuration there is provided a wearable item comprising:
a flexible base material forming at least a portion of the wearable item;
plural conductive traces traversing the flexible base material; and
conductivity sensing circuitry coupled to the plural conductive traces, wherein the conductivity sensing circuitry is configured to distinguish conductivity from non-conductivity of the plural conductive traces, and configured to generate a conductivity indication for at least one of the plural conductive traces,
and wherein the plural conductive traces follow indirect paths across the flexible base material, such that a conductive trace traversing the flexible base material from a first point to a second point has a trace length which is greater than a direct distance between the first point and the second point.

The present techniques support the monitoring of the integrity of a flexible base material, in particular where the flexible base material forms at least part of a wearable item. The flexible base material and the wearable item may each take a wide range of forms and the present techniques are not limited to any particular type of material or type of wearable item. Nevertheless, for the purposes of example illustration, wearable items such as protective gloves, condoms, or other personal protective equipment (PPE) may be envisaged, and thus correspondingly flexible base materials such as nitrile, latex and vinyl. The provision of plural conductive traces which traverse the flexible base material, where conductivity sensing circuitry is able to determine whether a given conductive trace is (currently) conductive or non-conductive, allows the integrity of the flexible base material to be inferred from the conductive state of the plural conductive traces. That is to say, when the set of plural conductive traces are all measured by the conductivity sensing circuitry as currently being "normally" conductive (in accordance with a predetermined expected conductivity for each trace), then in the situation where the flexible base material is sufficiently covered by the plural conductive traces, it may be inferred that the flexible base material is likely currently to be intact, since a rip in the flexible base material would very likely have also broken at least one of the plural conductive traces.

Despite the fine (i.e. thin and friable) nature of the conductive traces, the inherent flexibility of the base material need not generally jeopardise the integrity of the conductive traces, by virtue of the indirect paths which the conductive traces take when traversing the flexible material. Otherwise expressed, the conductive traces follow paths which may be called serpentine, meandering, snaking, or zigzag, in that in traversing the flexible material the path taken is longer, likely substantially longer, than the corresponding direct path. This arrangement allows a degree of stretching of the flexible material to be absorbed by a straightening of a conductive trace which generally extends in the direction of that stretching. In other words, the curves or meanders of the conductive traces straighten as the flexible material is stretched. It will be understood therefore that the degree to which the conductive traces are serpentine may be chosen to depend on the relative normal flexibility of the flexible base material. The more the flexible base material is required to stretch during normal use, the greater the degree of snaking of the conductive traces that may be required in order to accommodate that stretching.

In some example configurations the plural conductive traces comprise a first set of conductive traces and a second set of conductive traces, and wherein the conductivity sensing circuitry comprises:
driver circuitry configured to apply a test current to the first set of conductive traces;
readout circuitry configured to detect a current flow in the second set of conductive traces; and
control circuitry configured to control a set of trace connection switches, each trace connection switch arranged selectively to couple a pair of conductive traces comprising a first conductive trace of the first set of conductive traces and a second conductive trace of the second set of conductive traces,
wherein the conductivity sensing circuitry is configured to generate the conductivity indication for the pair of conductive traces.

This arrangement of the two sets of conductive traces and the provision of the driver, readout, and control circuitry enables the conductivity sensing with respect to conductive traces to be carried out with a significant degree of spatial granularity. Generally, in examples in which a given conductive trace is electrically independent of the other traces, when the conductivity sensing circuitry determines the conductivity of that conductive trace, an indication of a lack of conductivity can only be interpreted as showing that the conductive trace is likely broken at some unknown point along its length. However, the proposed arrangement of two sets of conductive traces, and the driver, readout, and control circuitry, means that, depending on the particular manner in which the two sets of conductive traces are laid out, spatial information regarding the location at which a lack of conductivity appears to be caused can be obtained. The present techniques are not limited to any particular physical arrangement of the two sets of conductive traces, yet for simplicity of explanation, and indeed providing an advantageously regular pattern of traces, a grid-like arrangement of the traces may be provided. Thus in one such example the driver circuitry is configured to apply the test current to a horizontally arranged first set of conductive traces, whilst the readout circuitry is configured to detect the current flow in a vertically arranged second set of conductive traces. Clearly the choice of orientation of horizontal and vertical traces is arbitrary and may be trivially switched or otherwise changed. Nevertheless, in this example selective enablement of individual trace connection switches can then allow a regularised grid-like probing of the intersections of the first set of conductive traces and the second set of conductive traces to be carried out.

The arrangement of the plural conductive traces may be variously provided, whether subdivided into sets of conductive traces or not. However, in some examples the plural conductive traces comprise a first set of conductive traces arranged on a first surface of the flexible base material and a second set of conductive traces arranged on a second surface of the flexible base material. This arrangement of sets of conductive traces arranged on opposite surfaces of the flexible base material may support an improved monitoring of the integrity of the flexible base material. For example, by correlating the conductivity indications for the first set of conductive traces with those of the second set of conductive traces, the likelihood of correct identification of an integrity breach of the flexible base material is improved.

In some examples the first surface of the flexible base material and the second set of conductive traces are an inner surface of the flexible base material and an outer surface of the flexible base material. Here the terms inner and outer are to be understood with reference to the fact that the flexible base material forms part of a wearable item, and therefore the inner and outer surfaces of the flexible base material are with respect to the as-worn state of the wearable item. In the example context of a latex glove, these would then be the inner surface of the latex which is in contact with the user's hand and the outer surface of the latex which generally faces away from the user's skin.

The present techniques are not limited to any particular groupings of the plural conductive traces, which may be provided in various configurations in accordance with the particular implementation. In some examples, the plural conductive traces comprise a third set of conductive traces and a fourth set of conductive traces, and wherein:

the driver circuitry is configured to apply a further test current to the third set of conductive traces;

the readout circuitry configured to detect a further current flow in the fourth set of conductive traces; and the control circuitry is configured to control a further set of further trace connection switches, each further trace connection switch arranged selectively to couple a further pair of conductive traces comprising a third conductive trace of the third set of conductive traces and a fourth conductive trace of the fourth set of conductive traces, wherein the conductivity sensing circuitry is configured to generate a further conductivity indication for the further pair of conductive traces. Thus for example a first and second set of conductive traces may provide the above described (logically) grid-like arrangement of conductive traces, whilst a third and fourth set of conductive traces may provide a further such arrangement, enabling the spatial granularity of identification achieved by each arrangement (first and second set of traces on the one hand and third and fourth set of traces on the other hand) to be correlated with one another and thus further improve the integrity monitoring.

In some such examples the first set of conductive traces and the second set of conductive traces are arranged on a first surface of the flexible base material, and the third set of conductive traces and the fourth set of conductive traces are arranged on a second surface of the flexible base material.

The monitoring of the conductivity indications from multiple sets of conductive traces may be provided in a variety of ways, but in some examples the wearable item further comprises rupture prediction circuitry configured to generate a potential rupture indication when:

the conductivity indication for the pair of conductive traces is indicative of non-conductivity;

the conductivity indication for the further pair of conductive traces is indicative of non-conductivity; and a trace connection switch for the pair of conductive traces and a trace connection switch for the further pair of conductive traces are within a predefined physical distance of one another. The predefined physical distance may be variously defined in dependence on the requirements of the integrity monitoring, the characteristics of the flexible material, the density of conductive traces provided, and so on.

The plural conductive traces and the conductivity sensing circuitry may be provided in accordance with any technically feasible process, but in some examples the plural conductive traces and the conductivity sensing circuitry are printed onto the flexible base material. Such a printed traces and circuitry may be particularly appropriate in the context of some wearable items for which the thin and flexible nature of the wearable item is key to its function, such as may be the case for gloves, and is notably the case for condoms.

A power source for the conductivity sensing circuitry of the wearable item may be provided in a variety of ways. In some examples the wearable item further comprises a printed battery integrated onto the flexible base material. In some examples the wearable item further comprises an energy harvester integrated onto the flexible base material. Such an energy harvester may take a variety of forms as appropriate to the nature of the wearable item, but in some examples the energy harvester is arranged to generate electrical energy triboelectrically. A triboelectrical energy harvester may for example be provided as a triboelectric nanogenerator in the form of a patch on the wearable item. The user could then activate the conductivity sensing circuitry of the wearable item, for example shortly after donning the wearable item, by appropriate stimulation (e.g. rubbing) of the patch. It is assumed that one of ordinary skill in the art will have no difficulty in envisaging the provision of such a patch as part of a wearable item such as a glove or a condom, and the various mechanisms via which the wearer of the item might then achieve the required friction with respect to the patch.

The conductivity indication may be made use of in a variety of ways, but in some examples the wearable item further comprises a display component controlled by the conductivity sensing circuitry, wherein the display component is configured to generate a visual indication of the conductivity the display component is an organic LED (light emitting diode).

Nevertheless, alternatively or in addition, the wearable item may communicate the conductivity indication to a further recipient. In some examples the wearable item further comprises communication circuitry configured to transmit a signal indicative of the conductivity indication for debug or testing purposes. This signal may therefore be made use of in various ways, although in particular by a person (e.g. an engineer) implementing these techniques, for example whereby the signal is received by a variety of computing device, enabling the person to study the behaviour of the wearable item and in particular the conductivity indication generation by the conductivity sensing circuitry.

Apart from test purposes the wearable item may also be configured to transmit a potential rupture indication signal and accordingly in some examples the wearable item further comprises communication circuitry configured to transmit a signal indicative of the potential rupture indication. This signal may be received by a variety of recipients, in particular dependent on the manner in which the potential rupture indication is intended to be communicated to a human user.

In some examples the communication circuitry is configured to transmit the signal indicative of the conductivity indication and/or the potential rupture indication via an NFC interface. This provides a useful short-range communication by which the signal indicative of the conductivity indication and/or the potential rupture indication can be communicated to a nearby device. Where the present techniques are provided in the context of the wearable item, this nearby device may usefully therefore be another item held or worn by the same user who wears the wearable item.

The communication of the signal may take place in various ways and in some examples the communication circuitry is configured to transmit the signal indicative of the potential rupture indication via body conductivity of a wearer of the wearable item. The inherent conductivity of the human body thereby provides a useful communication medium for the communication between two worn items.

In some examples the wearable item is one of:
a glove;
a condom; and
an item of personal protective equipment (PPE).

In accordance with one example configuration there is provided a system comprising:
one of the wearable items described above; and
a further wearable item,
wherein the wearable item and the further wearable item are arranged to be worn by an individual, and wherein the further wearable item is configured to receive the signal indicative of the potential rupture indication and to communicate the signal to the individual.

In accordance with one example configuration there is provided a method of monitoring a wearable item, wherein the wearable item comprises:
a flexible base material forming at least a portion of the wearable item; and
a first set of conductive traces and a second set of conductive traces traversing the flexible base material, wherein the first set of conductive traces and the second set of conductive traces follow indirect paths across the flexible base material, such that a conductive trace traversing the flexible base material from a first point to a second point has a trace length which is greater than a direct distance between the first point and the second point,
the method comprising the steps of:
applying a test current to the first set of conductive traces;
detecting a current flow in the second set of conductive traces;
controlling a set of trace connection switches, each trace connection switch arranged selectively to couple a pair of conductive traces comprising a first conductive trace of the first set of conductive traces and a second conductive trace of the second set of conductive traces; and
generate a conductivity indication for the pair of conductive traces.

Particular embodiments will now be described with reference to the figures.

FIG. 1 illustrates a wearable item 10 in accordance with one example configuration. The wearable item 10 in this example can be seen to be a glove. At the sleeve of the glove there is provided conductivity sensing circuitry 30 which is coupled to a number of conductive traces 20 which cover the surface of the material from which the glove is formed. The glove may for example be made of nitrile, latex, or vinyl. It can be seen that the conductive traces do not follow direct paths across the material of the glove and instead follow indirect serpentine paths which take an intentionally meandering path. These meandering paths allow the glove to be stretched, for example as it is put on, without the conductive traces being stretched to the point of breaking. The conductivity sensing circuitry is arranged to generate a conductivity indication for each the plural conductive traces, on the basis of whether each trace appears to be intact (i.e. conducting normally) or appears to be broken (in that it is not conducting). The particular manner in which this conductivity determination is made for each trace is not significant and may be carried out in any technically feasible manner with which the skilled person is familiar. The latex glove of FIG. 1 is just one example implementation of the present techniques and the conductive traces may equally well be provided on the flexible base material of other wearable items, such as a condom.

Figure 2:
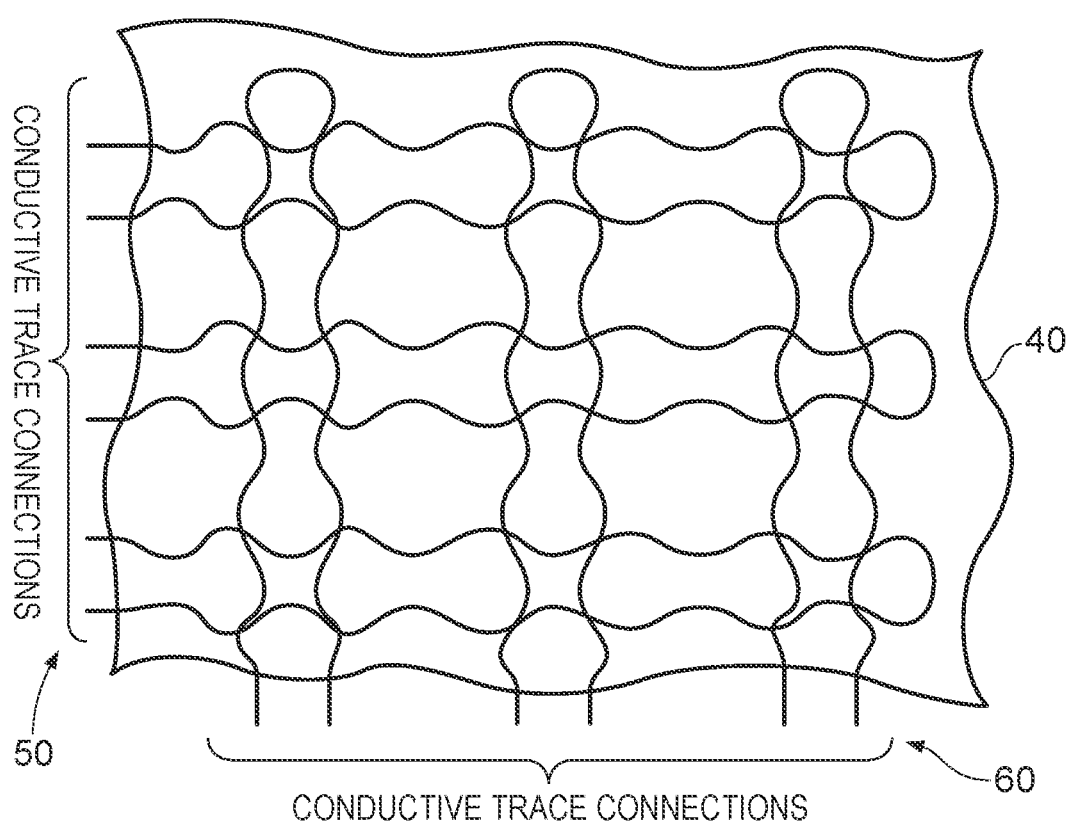
FIG. 2 schematically illustrates a section of flexible material having a number of conductive traces traversing the flexible material in accordance with some example configurations.

FIG. 2 schematically illustrates a section of flexible material having a number of conductive traces traversing the flexible material in accordance with some example configurations. Whilst generally the plural conductive traces traversing the flexible base material of the present techniques may be distributed in any configuration across the base material, the example of FIG. 2 shows a base material 40 on which a first set of conductive traces 50 are arranged generally horizontally (in the orientation shown) and a second set of conductive traces 60 are arranged generally vertically. The broadly orthogonal orientation of the two sets of conductive traces with respect to one another improves the spatial discrimination of the conductivity sensing circuitry (not shown) with regard to the position of non-conductivity points (i.e. potential integrity breaches of the flexible base material).

Figure 3:
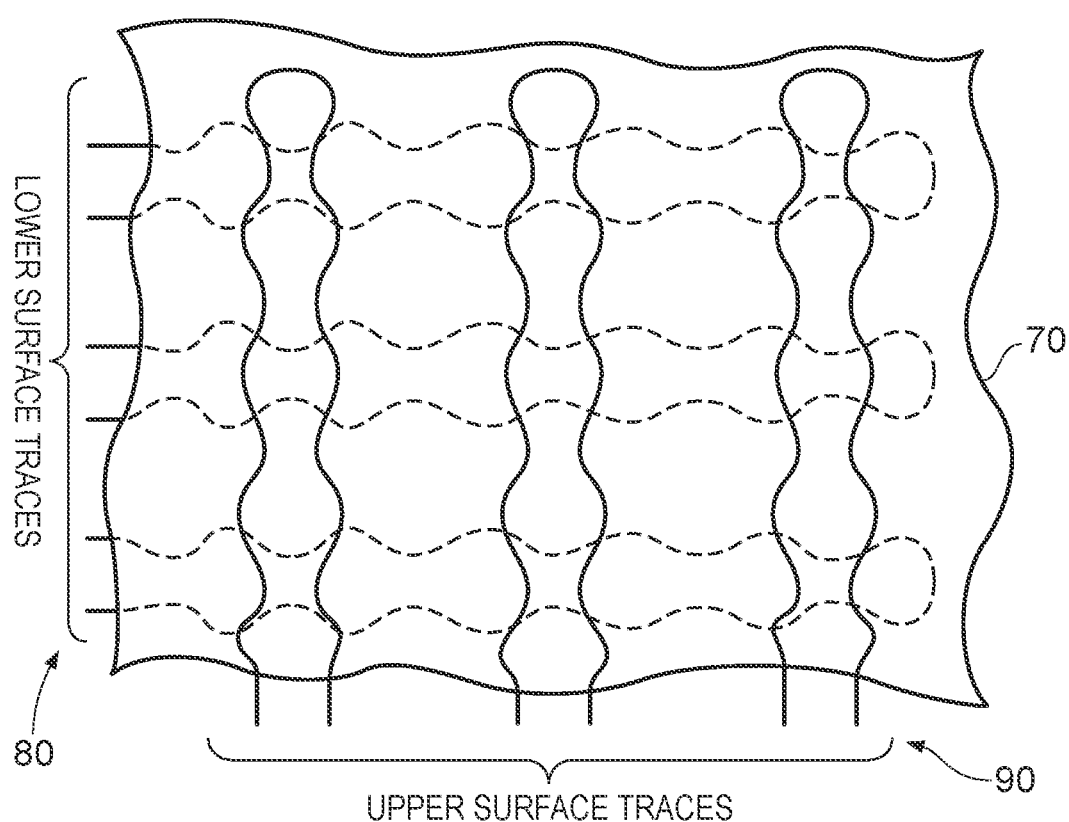
FIG. 3 schematically illustrates a section of flexible material having a number of conductive traces traversing the flexible material on its upper and lower surfaces in accordance with some example configurations.

FIG. 3 schematically illustrates a section of flexible material having a number of conductive traces traversing the flexible material, which is similar to the illustration of FIG. 2 although here the base material 70 is shown to carry a first (approximately horizontal) set of conductive traces 80 on its lower surface (i.e. the surface facing away from the viewer in the orientation shown) and a second set of conductive traces 90 are arranged generally vertically on its upper surface. As well as the broadly orthogonal orientation of the two sets of conductive traces with respect to one another, the arrangement of the two sets on opposite surfaces of the flexible base material supports improved integrity monitoring, since when a non-conductivity of one of the first set of traces (on the first surface) can be correlated with a non-conductivity of one of the second set of traces (on the second surface), there is a greater likelihood of identifying a rupture of the flexible base material, i.e. damage which has caused a through-hole in the material.

Figure 4:
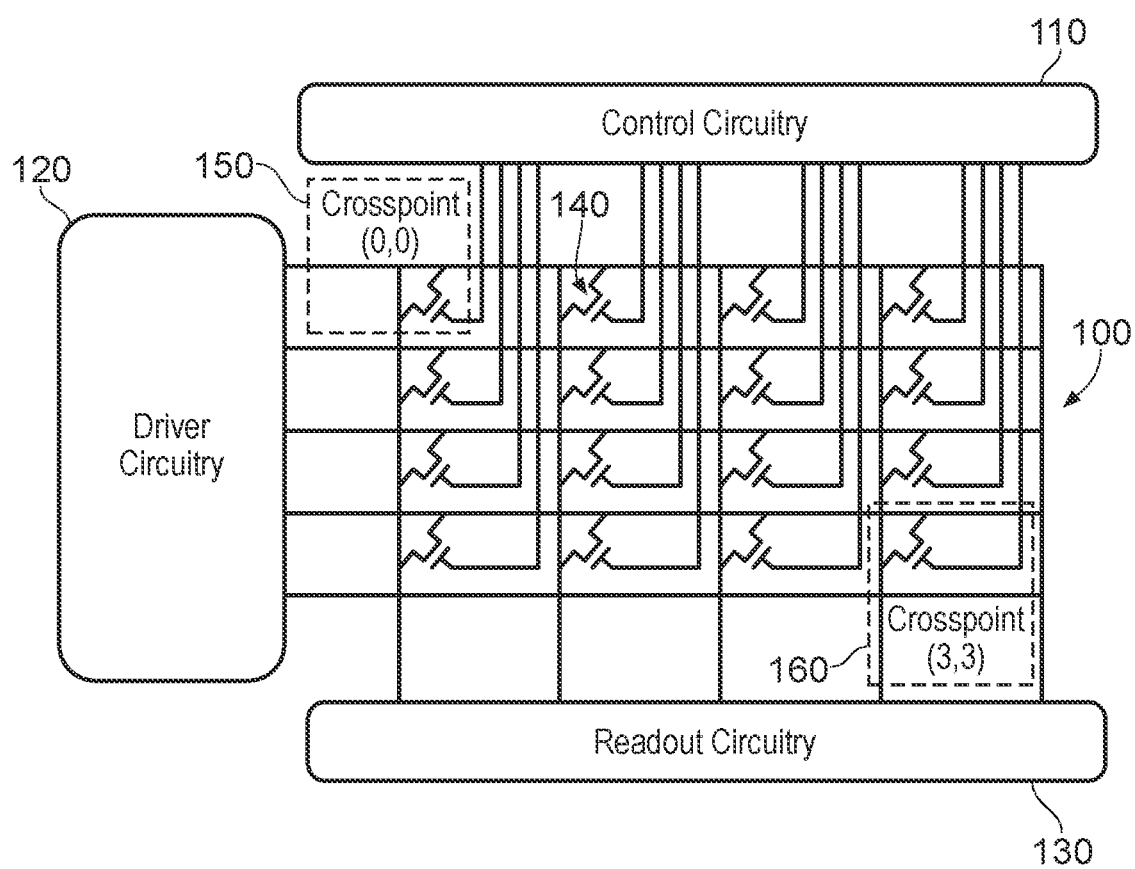
FIG. 4 schematically illustrates a network of conductive traces, control circuitry, driver circuitry, and readout circuitry in accordance with some example configurations.

FIG. 4 schematically illustrates a network 100 of conductive traces, control circuitry 110, driver circuitry 120, and readout circuitry 130 in accordance with some example configurations. The network 100 of conductive traces is arranged in an approximately grid-like pattern, i.e. with a first set of conductive traces running in one direction, whilst a second set of conductive traces runs in a second direction generally orthogonal to the first set. Further, the first set of conductive traces are coupled to driver circuitry 120, such that the driver circuitry 120 can selectively apply a test current to one of the first set of conductive traces. At each of the intersections (cross-points) of the first set of conductive traces and the second set of conductive traces there is provided a connection switch 140, each of which is individually controlled by the control circuitry 110. Accordingly, when the driver circuitry 120 applies a test current to one of the first (horizontal) set of conductive traces, the control circuitry 110 activates at least one of the connection switches 140 which are coupled to the conductive trace being driven by the driver circuitry 120, and the readout circuitry 130 then determines if a corresponding current flow is measured in the corresponding at least one of the second (vertical) set of conductive traces. In this manner each of the cross-points (intersections) can individually be probed to determine if normal current flow via that cross-point can be measured. Exemplary cross-points (0,0) 150 and (3,3) 160 are labelled in the figure. Generally, the control circuitry 110, driver circuitry 120, and readout circuitry 130 can be considered together to form an example of conductivity sensing circuitry which determines the conductivity of the plural conductive traces. The cross-bar approach to the probing of conductivity as illustrated in the example of FIG. 4 allows a spatial granularity of the conductivity to be determined at spacings given by the separation of the connection switches. Correspondingly information concerning the integrity of the flexible base material can be gained at the same spatial granularity.

Figure 5:
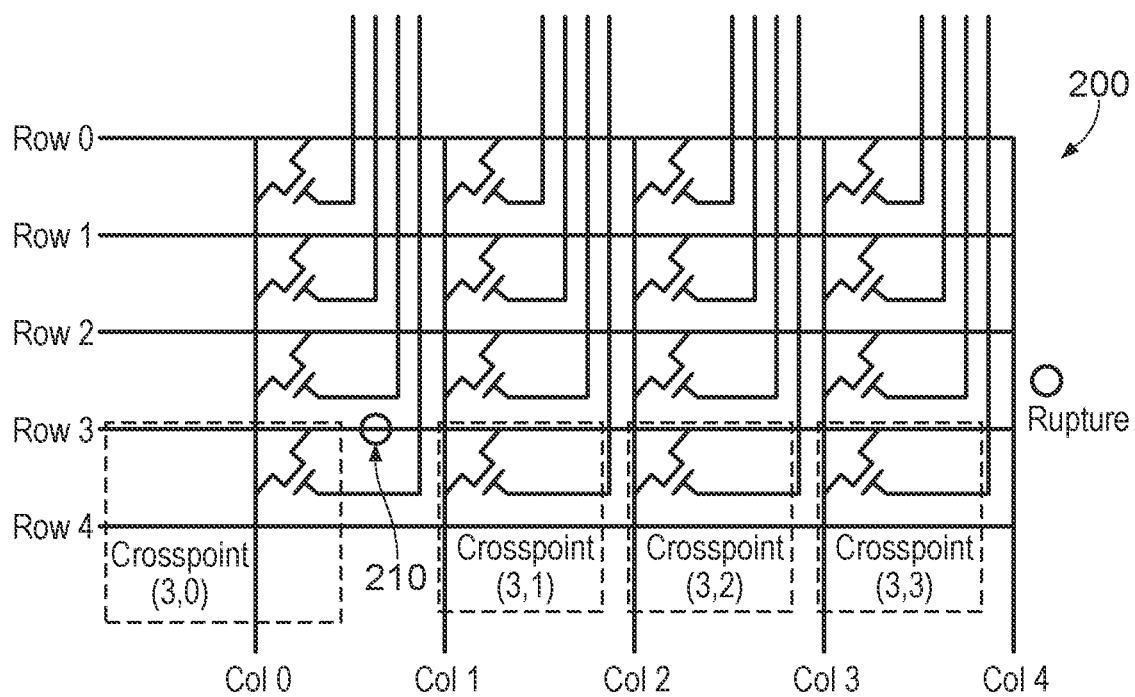
FIG. 5 schematically illustrates a network of conductive traces and the identification of a possible rupture location in accordance with some example configurations.

FIG. 5 schematically illustrates a network of conductive traces and the identification of a possible rupture location in accordance with some example configurations. In the network 200 illustrated only a set of conductive traces forming rows, a set of conductive traces forming columns, and the set of connection switches at the intersections between the rows and columns are shown. Control circuitry, driver circuitry, and readout circuitry should be understood to be present in this illustrated configuration, but has been omitted from this figure merely for clarity of illustration. The figure further indicates a rupture location 210, i.e. a point at which there is a break or puncture in the flexible base material on which the illustrated conductive traces and connection switches lie. In the example of FIG. 5 the rows of conductive traces are coupled to the driver circuitry and the columns of conductive traces are coupled to the readout circuitry as in the example of FIG. 4. Accordingly, when the driver circuitry applies the test current to the row 3 conductive trace, the cross-point (3,0) can successfully couple that test current to the column 0 conductive trace. However, the rupture interrupts the row 3 conductive trace to the right of cross-point (3,0), and thus when any of cross-points (3,1), (3,2), or (3,3) are activated none of them successfully couples the test current to any of the column 1, column 2, or column 3 conductive traces. Expressed the other way round, when the driver circuitry applies the test current to the row 3 conductive trace, and only the column 0 conductive trace conveys that test current to the readout circuitry, it can be inferred that there is a break in the row 3 conductive trace somewhere between cross-point (3,0) and cross-point (3,1), and therefore that a potential rupture of the flexible base material has occurred at this location.

Figure 6:
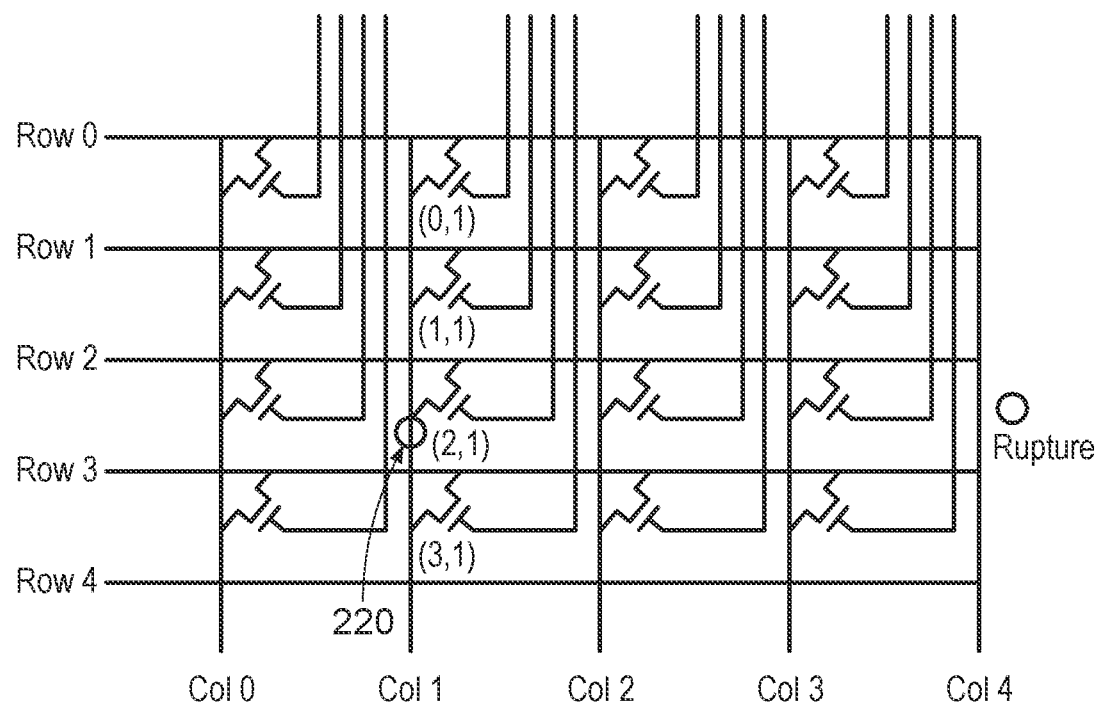
FIG. 6 schematically illustrates a network of conductive traces and the identification of a possible rupture location in accordance with some example configurations.

FIG. 6 schematically illustrates a network of conductive traces and the identification of a possible rupture location in accordance with some example configurations. The arrangement of conductive traces and cross-point connection switches is the same as that described above with reference to FIG. 5. However, in the example of FIG. 6 a different rupture location 220 is shown, which in this example lies on the column 1 conductive trace, midway between the row 2 and row 3 conductive traces. Accordingly, in this situation readout current will only be measured by the readout circuitry on conductive trace column 1 when the test current is applied by the driver circuitry on row 3 or row 4 (note that connection switches are not explicitly illustrated on row 4, but can be assumed). As such it can be inferred that there is a break in the column 1 conductive trace somewhere between cross-point (2,1) and cross-point (3,1), and therefore that a potential rupture of the flexible base material has occurred at this location.

Figure 7:
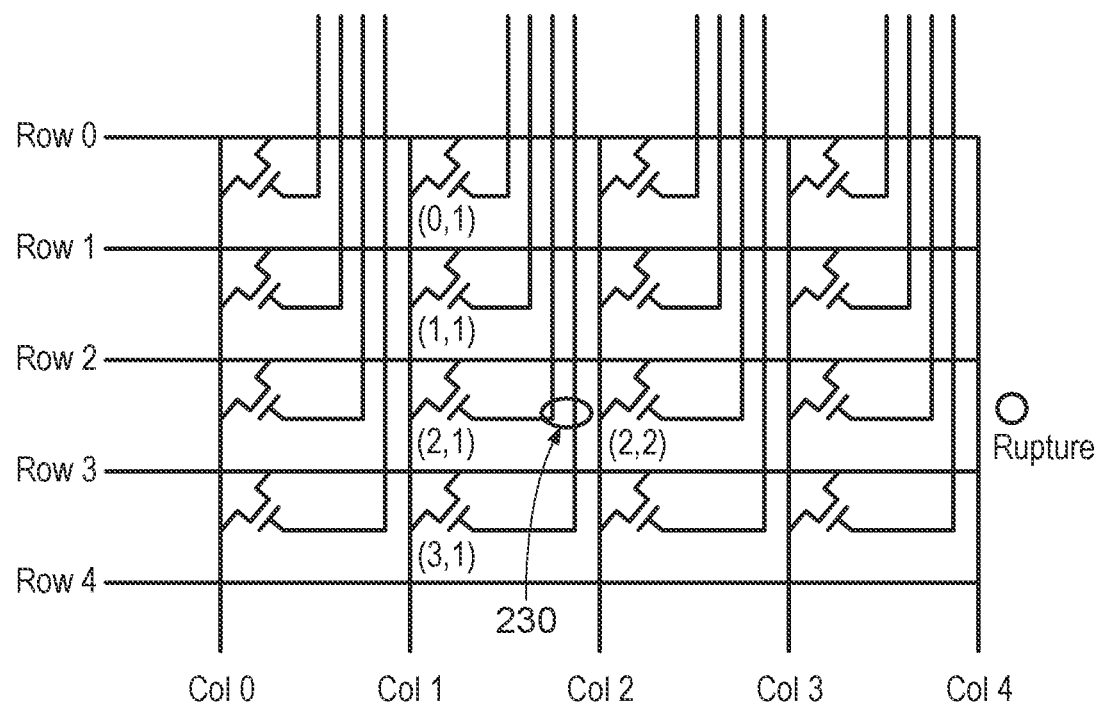
FIG. 7 schematically illustrates a network of conductive traces and the identification of a possible rupture location in accordance with some example configurations.

FIG. 7 schematically illustrates a network of conductive traces and the identification of a possible rupture location in accordance with some example configurations. The arrangement of conductive traces and cross-point connection switches is the same as that described above with reference to FIGS. 5 and 6. However, in the example of FIG. 7 a different rupture location 230 is shown, where here the rupture intersects the control lines via which the control circuitry (not shown, though understood to be connected to the switch control lines at the upper side of the figure) control the cross-point switches (2,1) and (3,1). Accordingly, assuming that the cross-point switches do not connect the row conductive traces to the column conductive traces unless they receive the control signal from the control circuitry, then in this situation readout current will only be measured by the readout circuitry on conductive trace column 1 when the test current is applied by the driver circuitry on row 0 or row 1. As such it can be inferred that there is either a break in the column 1 conductive trace somewhere between cross-point (1,1) and cross-point (2,1), or that (as is in fact the case as illustrated) that there is a break in the control lines which control the cross-point switches (2,1) and (3,1). Either way, it can be inferred that a potential rupture of the flexible base material has occurred at this approximate location.

Figure 8A:
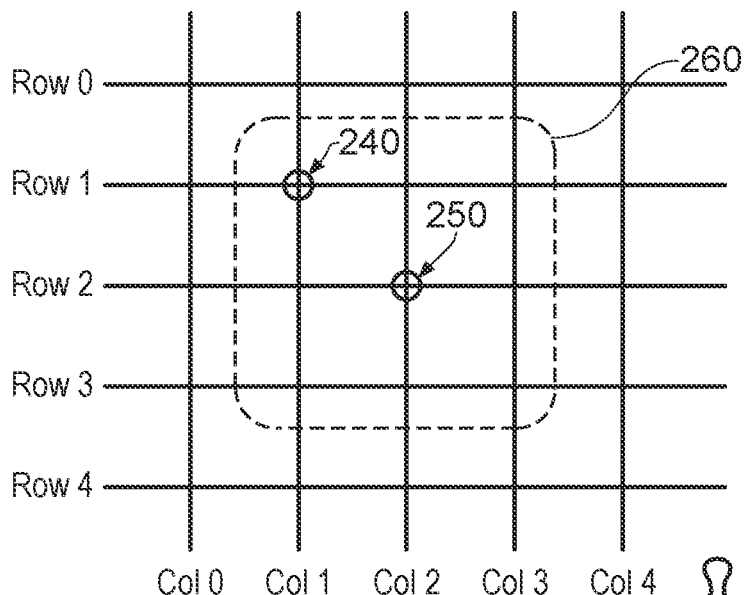
FIGS. 8A and 8B schematically illustrate the identification of a possible rupture location on the basis of spatially correlated non-conductivity signals in accordance with some example configurations.
Figure 8C:
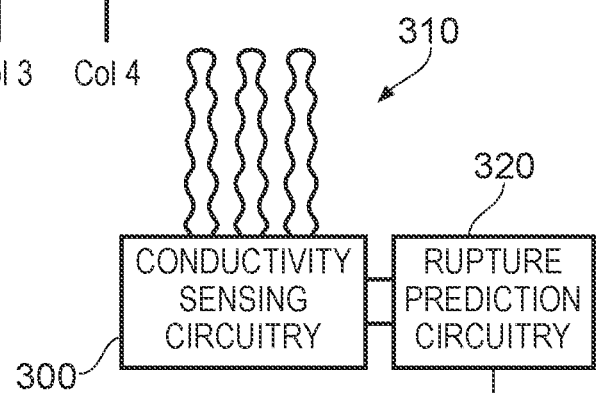
FIG. 8C schematically illustrates conductivity sensing circuitry, conductive traces, and rupture predication circuitry in accordance with some example configurations.
Figure 8B:
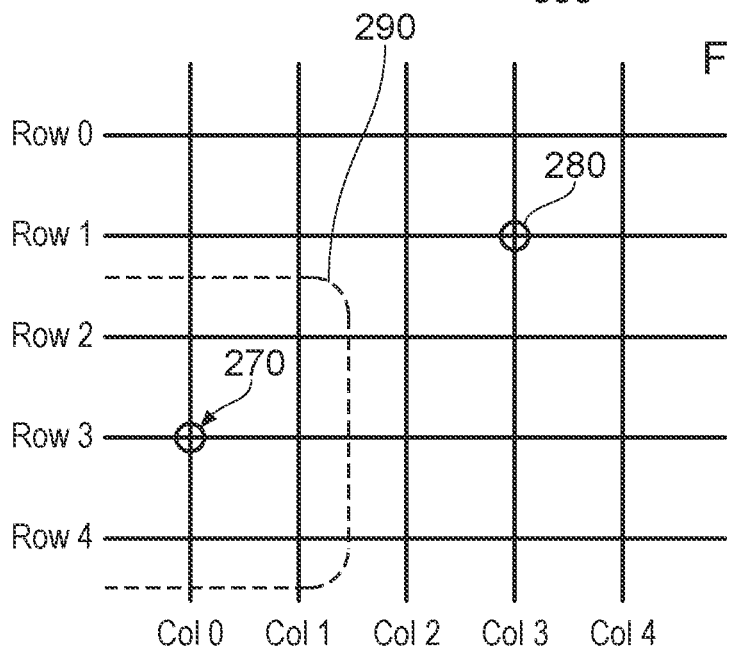

FIGS. 8A and 8B schematically illustrate the identification of a possible rupture location on the basis of spatially correlated non-conductivity signals in accordance with some example configurations. As in the cases of FIGS. 5-7 above the example of a set of 5 row conductive traces and a set of 5 column conductive traces is taken. In each case two identified conductivity interruptions are shown, 240 and 250 in FIG. 8A, and 270 and 280 in FIG. 8B. In each case the two points may be determined with respect to a single grid-like arrangement of conductivity traces on a single surface of the flexible base material, or each one may be determined with respect to one of two grid-like arrangements of conductivity traces, one on each surface of the flexible base material. The proximity of the two identified conductivity interruptions can then be used to determine if the situation is categorised as a potential rupture to the flexible base material. In FIG. 8A the dashed line 260 indicates a proximity boundary with respect to the position of point 250, within which the presence of another conductivity interruption is concluded to be indicative of a likely rupture of the flexible base material. Accordingly, the situation in FIG. 8A is interpreted as likely due to a rupture. By contrast, in the situation of FIG. 8B the boundary 290 with respect to one of the conductivity interruption points 270 does not encompass the other conductivity interruption point 280 and therefore the situation in FIG. 8B is not interpreted as likely due to a rupture.

FIG. 8C schematically illustrates conductivity sensing circuitry 300, conductive traces 310, and rupture predication circuitry 320 in accordance with some example configurations. With reference to the examples of FIGS. 8A and 8B, the conductivity sensing circuitry 300 determines the conductivity of the conductive traces 310 and when they are arranged in the grid-like pattern (and the conductivity sensing circuitry 300 comprises driver circuitry, control circuitry and readout circuitry as described) determines the locations of the conductivity interruption points. These indications of conductivity issues are passed to the rupture prediction circuitry 320, which combines the indications received (possibly from more than one surface of the flexible material) and correlates their locations to determine whether a rupture is judged to have occurred or not. A potential rupture signal is then generated when this is the case.

Figure 9A:
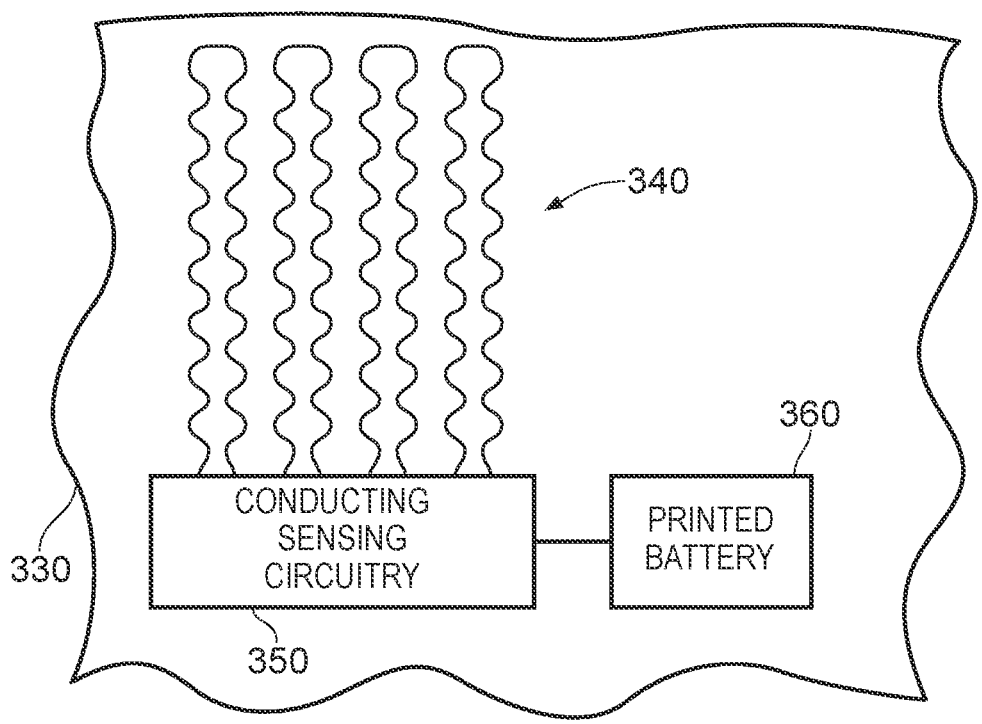
FIG. 9A schematically illustrates conductivity sensing circuitry, conductive traces, and a printed battery in accordance with some example configurations.

FIG. 9A schematically illustrates conductivity sensing circuitry, conductive traces, and a printed battery in accordance with some example configurations. A flexible base material 330 has components printed onto it, where in the illustrated example these are conductivity sensing circuitry 350, conductive traces 340, and a printed battery 360. It should be noted that this example is only presented in a generic configuration of conductivity sensing circuitry 350 and conductive traces 340 for clarity of illustration, but for example the printed traces may be configured in accordance with any of the various trace configurations (e.g. grid-like cross-bar arrangement) described herein, and similarly the conducting sensing circuitry may be configured in accordance with any of the various configurations described herein (e.g. comprising driver circuitry, control circuitry, and readout circuitry).

Figure 9B:
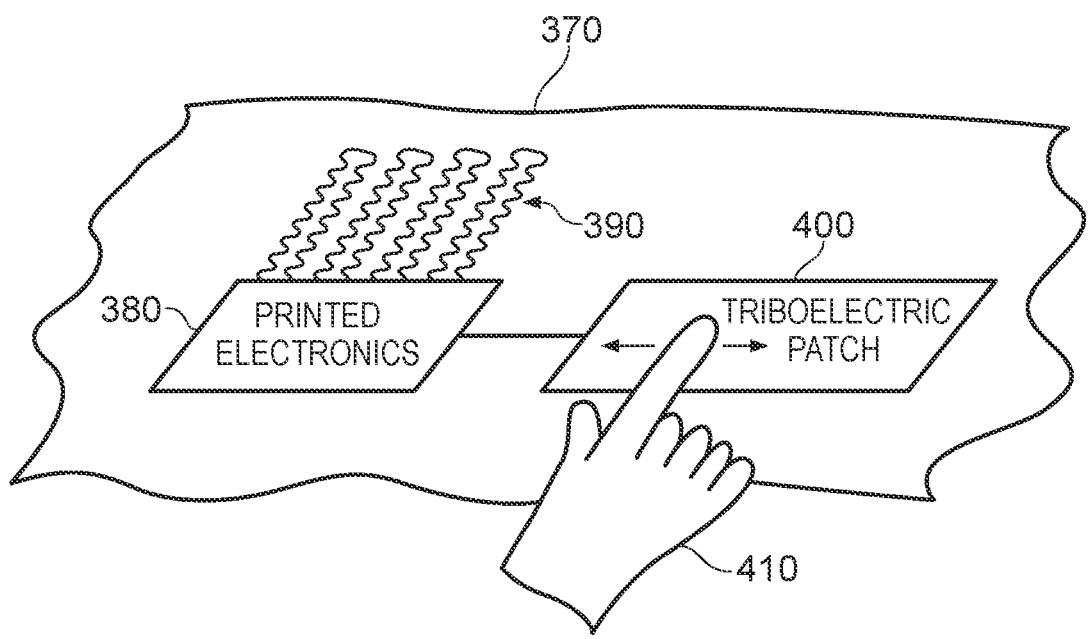
FIG. 9B schematically illustrates conductivity sensing circuitry, conductive traces, and a triboelectric patch in accordance with some example configurations.

FIG. 9B schematically illustrates conductivity sensing circuitry, conductive traces, and a triboelectric patch in accordance with some example configurations. A flexible base material 370 has components printed onto it, where in the illustrated example these are printed electronics (comprising conductivity sensing circuitry) 380, and conductive traces 390. In this example the power for the printed electronics 380 is provided by the triboelectric patch 400, wherein friction applied to the patch by a user 410 (e.g. by a brisk rubbing with a finger) causes electric charge to be released, which is converted into a small, but finite electrical supply. The flexible base material 370 may form part of any suitable wearable item and consequently the triboelectric patch 400 can be suitably placed for convenient stimulation by the user, e.g. on a sleeve section of a glove. Once more it should be noted that this example is only presented in a generic configuration of the printed electronics 380 and conductive traces 390 for clarity of illustration, but the printed traces may be configured in accordance with any of the various trace configurations (e.g. grid-like cross-bar arrangement) described herein, and similarly the printed electronics (conducting sensing circuitry) may be configured in accordance with any of the various configurations described herein (e.g. comprising driver circuitry, control circuitry, and readout circuitry).

Figure 10A:
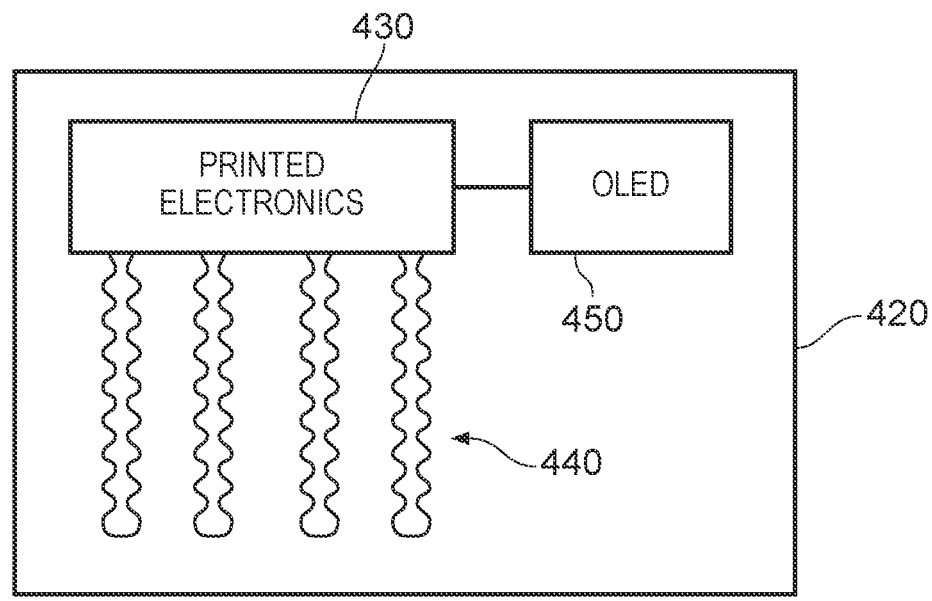
FIG. 10A schematically illustrates conductivity sensing circuitry, conductive traces, and an OLED in accordance with some example configurations.

FIG. 10A schematically illustrates conductivity sensing circuitry, conductive traces, and an OLED in accordance with some example configurations. A flexible base material 420 has components printed onto it, where in the illustrated example these are printed electronics (comprising conductivity sensing circuitry) 430, and conductive traces 440. This example further illustrates an OLED (organic light emitting diode) device 450 coupled to the printed electronics 430, which serves as a mechanism by which a conductivity indication and/or a possible rupture indication can be communicated to the user. To take the example of the wearable item being a glove, where the conductive traces 440 substantially cover the "hand" portion of the glove, the printed electronics 430 and the OLED 450 may be positioned on a sleeve portion of the glove. When the user puts the glove on for the first time, the electronic circuitry can be activated (either by stimulation of a triboelectric patch, as in the case of FIG. 9B, or by another simple contact activation mechanism when a printed battery is provided) and the state of the OLED can communicate the determined integrity status of the glove to the user. Were the OLED to indicate a suspected integrity breach (i.e. rupture), the user might choose to dispose of this pair of gloves, and put on a replacement pair.

Figure 10B:
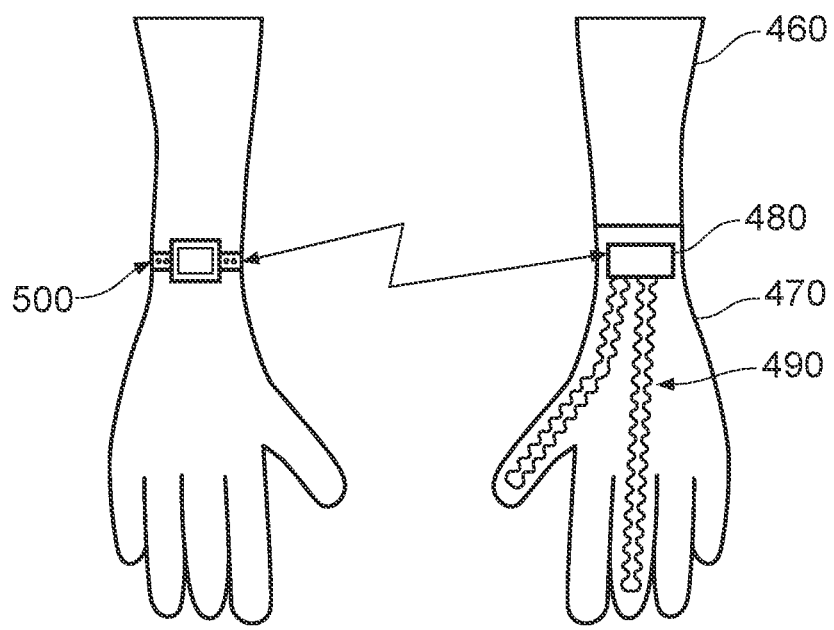
FIG. 10B schematically illustrates a wearable item comprising a flexible base material with conductive traces in communication with another wearable item in accordance with some example configurations.

FIG. 10B schematically illustrates a wearable item comprising a flexible base material with conductive traces in communication with another wearable item in accordance with some example configurations. A user 460 is shown to be wearing a glove 470, which in accordance with the present techniques is provided with printed electronics (comprising conductivity sensing circuitry) 480 coupled to conductive traces 490 which cover the surface of the glove (only two conductive traces 490 are explicitly shown in FIG. 10B for clarity of illustration). The user 460 is also wearing a further wearable item, which in this case is a smartwatch 500. The printed electronics 480 are provided with a communications component, allowing a conductivity indication and/or a possible rupture indication to be sent by a signal to a recipient, which in this example is the smartwatch 500. This communication may take place via various media. In one example, communications component of the printed electronics 480 comprises an NFC (near-field communication) interface, allowing communication with another device having such an interface (e.g. the smartwatch 500). In another example, both the printed electronics 480 and the smartwatch 500 have electrical contacts in direct contact with the skin of the user 460, and the conductivity of the user's skin is employed as the communication medium. Further, whilst in this example the recipient of devices smartwatch 500, any other wearable or portable device belonging to a user might be the signal recipient, for example the user's smartphone (itself having suitable communications capability such as NFC).

Figure 11:
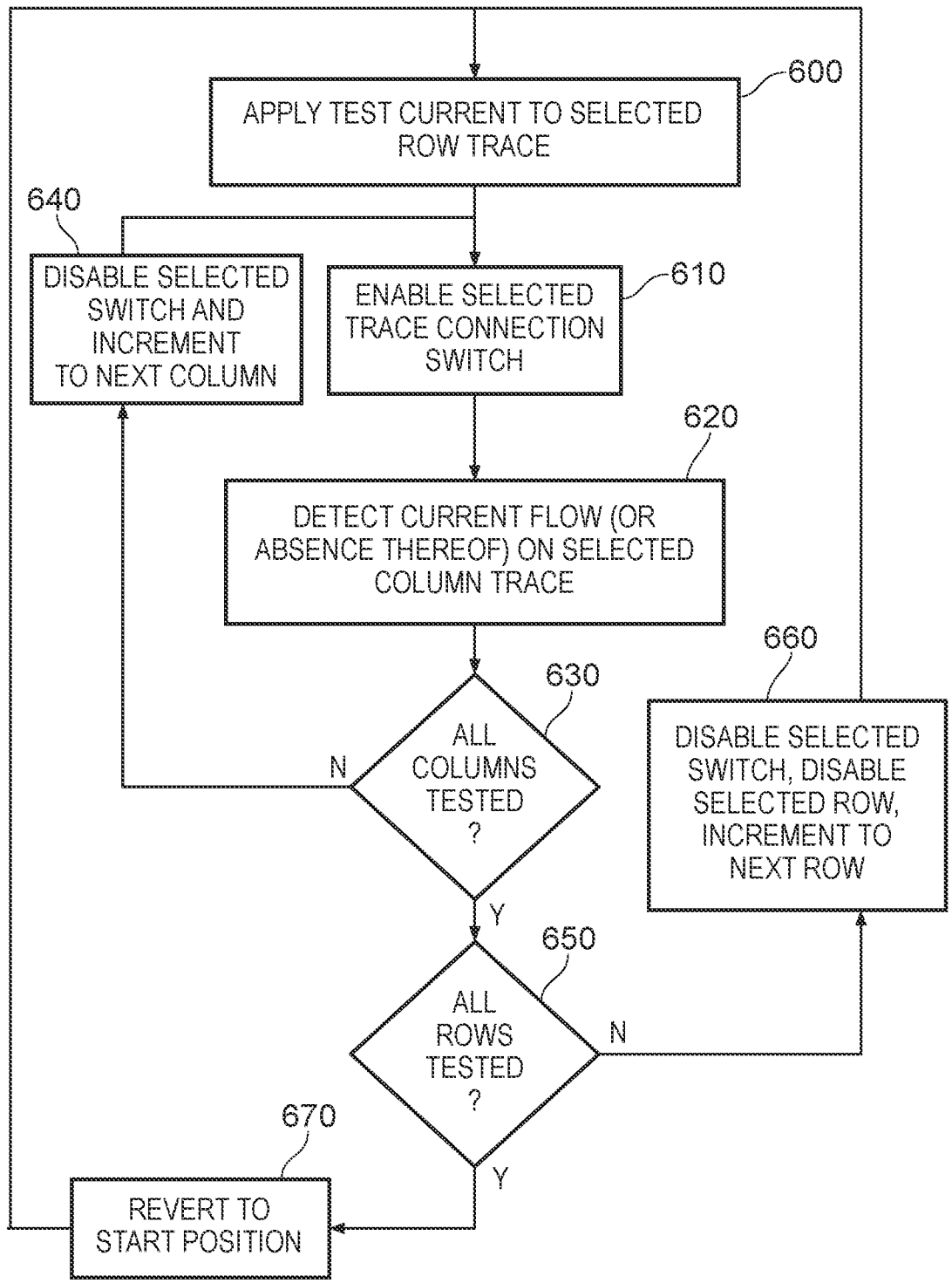
FIG. 11 is a flow diagram showing a sequence of steps which are taken in accordance with the method of some example configurations.

FIG. 11 is a flow diagram showing a sequence of steps which are taken in accordance with the method of some example configurations. This method may for example be applied to example configurations such as that schematically illustrated in FIG. 4, i.e. where the conductive traces are arranged in a grid-like manner, and driver circuitry control circuitry and readout circuitry provide supporting electronics for the conductivity of the conductive traces to be probed in a systematic, spatially granular manner. The flow can be considered to begin at step 600 where driver circuitry applies a test current to a selected row conductive trace. The control circuitry then, at step 610, enables a selected trace connection switch which is coupled to the selected row conductive trace. At step 620 it is then determined (by means of readout circuitry) whether or not a corresponding current flow can be detected on the corresponding selected column conductive trace. Next at step 630 if all columns have not yet been tested for this row conductive trace then the flow proceeds via step 640, where the just-tested trace connection switch is disabled and the testing increments to the next column. The flow then continues via step 610, where that next column is tested (by means of the corresponding trace connection switch being enabled and so on). Once it is determined at step 630 that all columns have been tested for this row conductive trace, it is then determined at step 650 whether all rows have been tested. If this is not the case, then the flow returns via step 660 at which the just-tested trace connection switch is disabled, the test current is removed from the just-tested row conductive trace, and the testing increments to the next row. The flow then continues via step 600, where that next row is tested. Once it is determined at step 650 that all rows have been tested, the flow proceeds to step 670, where the testing procedure is reverted to its starting position and a full scan of the grid may be restarted. It is an implementation detail whether any delay at step 670 is introduced, or whether the conductivity testing is essentially continuous.

In brief overall summary wearable items and methods of monitoring wearable items are disclosed. The wearable item comprises s flexible base material forming at least a portion of the wearable item, plural conductive traces traversing the flexible base material, and conductivity sensing circuitry coupled to the plural conductive traces. The conductivity sensing circuitry is configured to distinguish conductivity from non-conductivity of the plural conductive traces, and configured to generate a conductivity indication for at least one of the plural conductive traces. The plural conductive traces follow indirect paths across the flexible base material, allowing the flexible material to flex and stretch normally without breaking the conductive traces.

In the present application, the words "configured to . . ." are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope of the invention as defined by the appended claims. For example, various combinations of the features of the dependent claims could be made with the features of the independent claims without departing from the scope of the present invention.

We claim:

1. A wearable item comprising:
a flexible base material forming at least a portion of the wearable item;
plural conductive traces traversing the flexible base material; and
conductivity sensing circuitry coupled to the plural conductive traces, wherein the conductivity sensing circuitry is configured to distinguish conductivity from non-conductivity of the plural conductive traces, and configured to generate a conductivity indication for at least one of the plural conductive traces,
and wherein the plural conductive traces follow indirect paths across the flexible base material, such that a conductive trace traversing the flexible base material from a first point to a second point has a trace length which is greater than a direct distance between the first point and the second point,
wherein the plural conductive traces comprise a first set of conductive traces and a second set of conductive traces, and wherein the conductivity sensing circuitry comprises:
driver circuitry configured to apply a test current to the first set of conductive traces;
readout circuitry configured to detect a current flow in the second set of conductive traces; and
control circuitry configured to control a set of trace connection switches, each trace connection switch arranged selectively to couple a pair of conductive traces comprising a first conductive trace of the first set of conductive traces and a second conductive trace of the second set of conductive traces,
wherein the conductivity sensing circuitry is configured to generate the conductivity indication for the pair of conductive traces.

2. The wearable item as claimed in claim 1, wherein the first set of conductive traces are arranged on a first surface of the flexible base material and the second set of conductive traces are arranged on a second surface of the flexible base material.

3. The wearable item as claimed in claim 2, wherein the first surface of the flexible base material and the second set of conductive traces are an inner surface of the flexible base material and an outer surface of the flexible base material.

4. The wearable item as claimed in claim 1, wherein the plural conductive traces comprise a third set of conductive traces and a fourth set of conductive traces, and wherein:
the driver circuitry is configured to apply a further test current to the third set of conductive traces;
the readout circuitry configured to detect a further current flow in the fourth set of conductive traces; and
the control circuitry is configured to control a further set of further trace connection switches, each further trace connection switch arranged selectively to couple a further pair of conductive traces comprising a third conductive trace of the third set of conductive traces and a fourth conductive trace of the fourth set of conductive traces,
wherein the conductivity sensing circuitry is configured to generate a further conductivity indication for the further pair of conductive traces.

5. The wearable item as claimed in claim 4, wherein the first set of conductive traces and the second set of conductive traces are arranged on a first surface of the flexible base material, and wherein the third set of conductive traces and the fourth set of conductive traces are arranged on a second surface of the flexible base material.

6. The wearable item as claimed in claim 4, further comprising rupture prediction circuitry configured to generate a potential rupture indication when:
the conductivity indication for the pair of conductive traces is indicative of non-conductivity;
the conductivity indication for the further pair of conductive traces is indicative of non-conductivity; and
a trace connection switch for the pair of conductive traces and a trace connection switch for the further pair of conductive traces are within a predefined physical distance of one another.

7. The wearable item as claimed in claim 1, wherein the plural conductive traces and the conductivity sensing circuitry are printed onto the flexible base material.

8. The wearable item as claimed in claim 1, further comprising a printed battery integrated onto the flexible base material.

9. The wearable item as claimed in claim 1, further comprising an energy harvester integrated onto the flexible base material.

10. The wearable item as claimed in claim 9, wherein the energy harvester is arranged to generate electrical energy triboelectrically.

11. The wearable item as claimed in claim 1, further comprising a display component controlled by the conductivity sensing circuitry, wherein the display component is configured to generate a visual indication of the conductivity indication.

12. The wearable item as claimed in claim 11, wherein the display component is an organic LED.

13. The wearable item as claimed in claim 1, further comprising communication circuitry configured to transmit a signal indicative of the conductivity indication for debug or testing purposes.

14. The wearable item as claimed in claim 6, further comprising communication circuitry configured to transmit a signal indicative of the potential rupture indication.

15. The wearable item as claimed in claim 14, wherein the communication circuitry is configured to transmit the signal indicative of the conductivity indication and/or the potential rupture indication via an NFC interface.

16. The wearable item as claimed in claim 14, wherein the communication circuitry is configured to transmit the signal indicative of the potential rupture indication via body conductivity of a wearer of the wearable item.

17. The wearable item as claimed in claim 1, wherein the wearable item is one of:
   a glove;
   a condom; and
   an item of personal protective equipment (PPE).

18. A system comprising:
   the wearable item as claimed in claim 15; and
   a further wearable item,
   wherein the wearable item and the further wearable item are arranged to be worn by an individual, and wherein the further wearable item is configured to receive the signal indicative of the potential rupture indication and to communicate the signal to the individual.

19. A method of monitoring a wearable item, wherein the wearable item comprises:
   a flexible base material forming at least a portion of the wearable item; and
   a first set of conductive traces and a second set of conductive traces traversing the flexible base material,
   wherein the first set of conductive traces and the second set of conductive traces follow indirect paths across the flexible base material, such that a conductive trace traversing the flexible base material from a first point to a second point has a trace length which is greater than a direct distance between the first point and the second point, the method comprising the steps of:
   applying a test current to the first set of conductive traces;
   detecting a current flow in the second set of conductive traces;
   controlling a set of trace connection switches, each trace connection switch arranged selectively to couple a pair of conductive traces comprising a first conductive trace of the first set of conductive traces and a second conductive trace of the second set of conductive traces; and
   generate a conductivity indication for the pair of conductive traces.

* * * * *